United States Patent [19]

Ushioda et al.

[11] Patent Number: 5,032,314
[45] Date of Patent: Jul. 16, 1991

[54] OPTICALLY ACTIVE 2-SUBSTITUTED-PROPYL ETHER AND A LIQUID CRYSTAL COMPOSITION

[75] Inventors: Makoto Ushioda; Shinichi Saito; Kouji Ohno; Kazutoshi Miyazawa; Hiromichi Inoue, all of Kanagawa, Japan

[73] Assignee: Chisso Corporation, Ohsaka, Japan

[21] Appl. No.: 152,421

[22] Filed: Feb. 4, 1988

[30] Foreign Application Priority Data

Feb. 5, 1987 [JP] Japan .................................. 62-25234

[51] Int. Cl.$^5$ .................. C09K 19/12; G02F 1/13; C07C 69/76; C07C 67/02
[52] U.S. Cl. .......................... 252/299.65; 252/299.6; 252/299.61; 252/299.63; 252/299.66; 350/350 S; 560/59; 560/62; 560/73; 560/255
[58] Field of Search .................... 252/299.01, 299.61, 252/299.63, 299.6, 299.65, 299.67, 299.66; 350/350.5; 560/59, 62, 73, 254, 255

[56] References Cited

U.S. PATENT DOCUMENTS

| | | | |
|---|---|---|---|
| 4,576,727 | 12/1985 | Walba | 252/299.01 |
| 4,725,688 | 2/1988 | Taguchi et al. | 252/299.61 |
| 4,820,839 | 4/1989 | Krause et al. | 252/299.61 |
| 4,834,904 | 5/1989 | Krause et al. | 252/299.61 |

FOREIGN PATENT DOCUMENTS

| | | |
|---|---|---|
| 255219 | 2/1988 | European Pat. Off. . |
| 3515373 | 11/1986 | Fed. Rep. of Germany ................. 252/299.61 |
| 2181429 | 4/1987 | United Kingdom ........... 252/299.65 |
| 87/05012 | 8/1987 | World Int. Prop. O. . |

*Primary Examiner*—John S. Maples
*Assistant Examiner*—Philip Tucker
*Attorney, Agent, or Firm*—Wenderoth, Lind & Ponack

[57] ABSTRACT

A compound capable of shortening the response time of liquid crystal display elements and a composition containing the same are provided, which compound is expressed by the formula

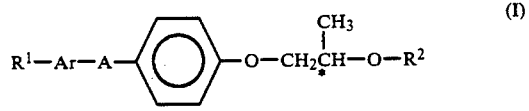
(I)

wherein $R^1$ represents a linear or branched chain alkyl group or alkoxy group, each of 1C–18C; Ar represents

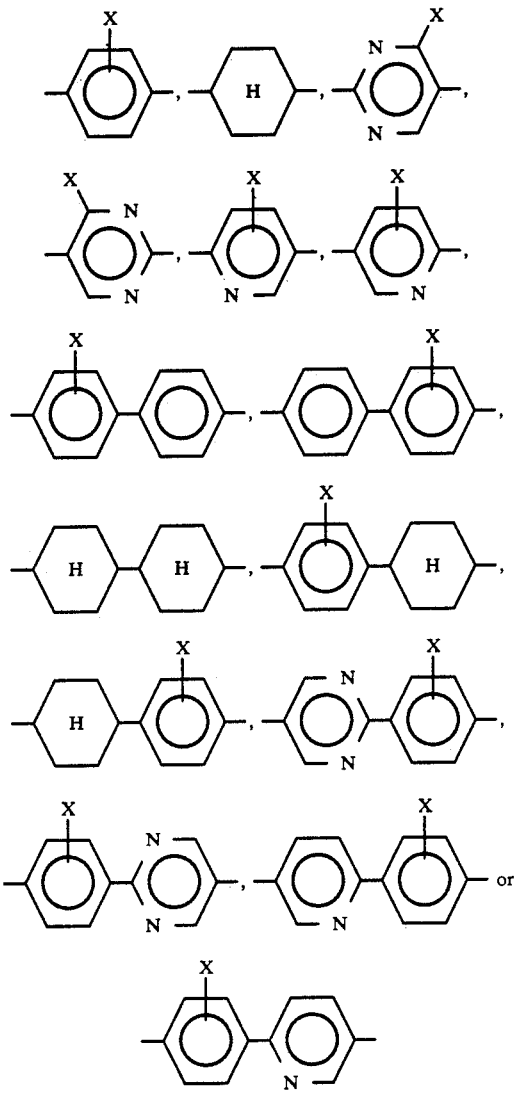

wherein X represents H, halogen atom, cyano group or methyl; A represents —COO— or —CH$_2$O—; $R^2$ represents a C$_1$–C$_{18}$ alkyl, A C$_2$–C$_{18}$ alkanoyl, a C$_3$–C$_{18}$ alkoxycarbonyl or a C$_4$–C$_{18}$ 2-alkoxypropanoyl; C having a symbol * attached thereonto represents asymmetric carbon atom; and when $R^2$ represents a linear chain alkyl and A represents —COO—, Ar is not

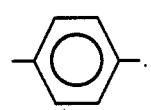

8 Claims, No Drawings

OPTICALLY ACTIVE 2-SUBSTITUTED-PROPYL ETHER AND A LIQUID CRYSTAL COMPOSITION

BACKGROUND OF THE INVENTION

1. Field of the Invention

This invention relates to a novel optically active liquid crystal substance and a liquid crystal composition containing the same; and more particularly it relates to a chiral liquid crystal substance having an optically active group and a ferroelectric liquid crystal composition containing the same.

2. Description of the Related Art

At present, ferroelectric liquid crystals have been noted as a display element material. This display mode utilizes phases of chiral smectic C, F, G, H, I, etc. Materials suitable to this display mode have been reported by various publications, but materials shortening the response time of the element have not yet been found.

SUMMARY OF THE INVENTION

The object of the present invention is to provide a compound shortening the response time of liquid crystal display elements and a liquid crystal composition containing the same.

The present invention resides in
a compound expressed by the formula (I)

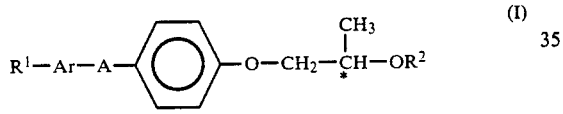

wherein $R^1$ represents a linear or branched chain alkyl group or alkoxy group, each of 1 to 18 carbon atoms; Ar represents

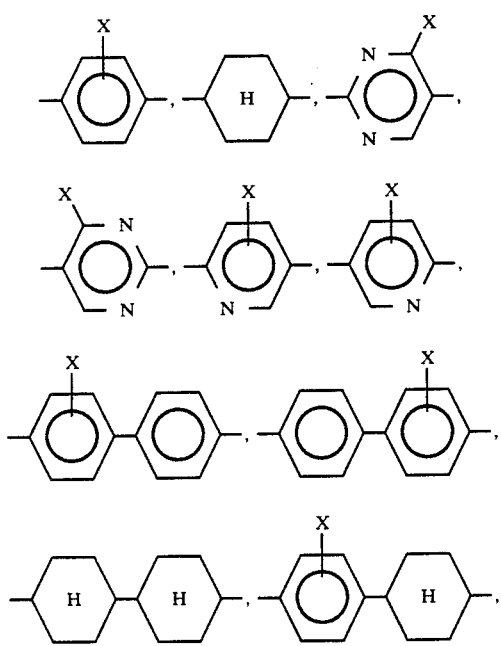

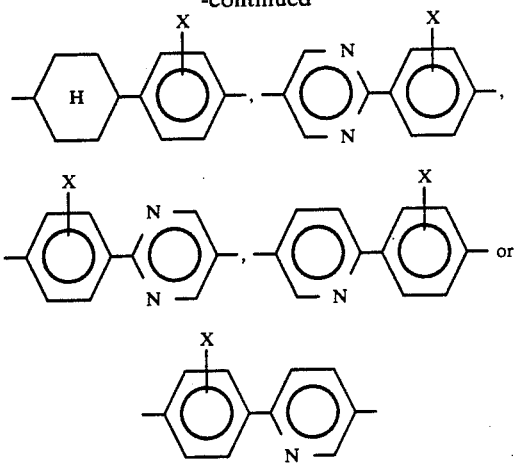

wherein X represents hydrogen atom, halogen atom, cyano group or methyl group; A represents -COO- or -CH$_2$O-; $R^2$ represents an alkyl group of 1 to 18 carbon atoms, an alkanoyl group of 2 to 18 carbon atoms, an alkoxycarbonyl group of 3 to 18 carbon atoms or a 2-alkoxypropanoyl group of 4 to 18 carbon atoms; C having a symbol * attached thereonto represents asymmetric carbon atom; and when $R^2$ represents a linear chain alkyl group and A represents -COO-, Ar is not

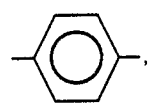

and a ferroelectric liquid crystal composition containing the compound of the formula (I) and further a light-switching element including the above-mentioned liquid crystal composition.

DETAILED DESCRIPTION OF PREFERRED EMBODIMENT

In the formula (I), $R^1$ represents preferably a linear chain alkyl or alkoxy group each of 4 to 14 carbon atoms; $R^2$ represents preferably an alkyl group of 2 to 14 carbon atoms, an alkanoyl group of 3 to 14 carbon atoms, an alkoxycarbonyl group of 3 to 14 carbon atoms or a 2-alkoxypropanoyl group of 4 to 14 carbon atoms, and $R^2$ which is optically active is more preferred.

A compound having a structure similar to that of the present invention is disclosed in U.S. Pat. 4,556,727. The compound is expressed by the formula

wherein R represents a lower alkyl group of 1 to 3 carbon atoms and R' represents an alkyl group of 9 to 12 carbon atoms. However, the compound of the present invention has a larger spontaneous polarization value (Ps) than that of the above compound and is useful for obtaining a liquid crystal element having a higher response rate than that of the above depicted compound.

The phase transition points of representative examples of the compound of the present invention are shown in Table 1.

TABLE 1

| Compound No. | In formula (I) Ar | B | R² | R¹ | Absolute configuration | Phase transition point (°C) Cr | SE | SB | Sc* | SA | Ch | Is | Note |
|---|---|---|---|---|---|---|---|---|---|---|---|---|---|
| 1 | (biphenyl) | —COO— | —C₂H₅ | C₈H₁₇O— | S | • 73.0 | — | • 100.0 | • 132.5 | • 176.0 | — | • | Example 1 |
| 2 | (biphenyl) | —COO— | —C₂H₅ | C₈H₁₇— | S | • 73.0 | — | • 91.8 | — | • 139.8 | — | • | Example 1 |
| 3 | (pyrimidine-phenyl) | —COO— | —C₄H₉ | C₈H₁₇— | R | • 65.5 | — | — | — | • 113.8 | — | • | |
| 4 | (pyridine-phenyl) | —COO— | —C₄H₉ | C₃H₇— | R | • 108.3 | — | — | — | — | (• 103.0) | • | |
| 5 | (biphenyl) | —COO— | —C₄H₉ | C₉H₁₉—O— | R | • 79.9 | • 80.5 | — | • 135.6 | • 157.9 | — | • | |
| 6 | (cyclohexyl-cyclohexyl) | —COO— | —C₄H₉ | C₅H₁₁ | R | • 29.8 | — | • 150.8 | — | — | — | • | |
| 7 | (fluorophenyl) | —COO— | —C₄H₉ | C₈H₁₇—O— | R | • 33.3 | — | — | — | — | — | • | |
| 8 | (biphenyl) | —COO— | —C(=O)—C₃H₇ | C₆H₁₃—O— | S | • 97.4 | (• 82.4) | • 108.9 | — | • 163.8 | — | • | Example 2 |

TABLE 1-continued

| Compound No. | In formula (I) R¹ | Ar | B | R² | Absolute configuration | Phase transition point (°C.) Cr | SE | SB | Sc* | SA | Ch | Is | Note |
|---|---|---|---|---|---|---|---|---|---|---|---|---|---|
| 9 | $C_9H_{19}$ | biphenyl | —COO— | $-\overset{O}{\underset{\parallel}{C}}-C_3H_7$ | S | • 74.1 | — | • 79.6 | — | • 115.9 | — | • | Example 2 |
| 10 | $C_{10}H_{21}-O-$ | biphenyl | —COO— | $-\overset{O}{\underset{\parallel}{C}}-C_4H_9$ | S | • 108.1 | — | — | • 117.0 | • 137.8 | — | • | Example 2 |
| 11 | $C_7H_{15}-$ | biphenyl | —COO— | $-\overset{O}{\underset{\parallel}{C}}-C_4H_9$ | S | • 67.9 | — | • 88.8 | — | • 117.7 | — | • | Example 2 |
| 12 | $C_8H_{17}-O-$ | biphenyl | —COO— | $-\overset{O}{\underset{\parallel}{C}}-C_6H_{13}$ | S | • 108.0 | — | — | — | • 139.0 | — | • | Example 2 |
| 13 | $C_5H_{11}-$ | dicyclohexyl | —COO— | $-\overset{O}{\underset{\parallel}{C}}-C_4H_9$ | S | • 61.7 | — | • 137.9 | — | — | — | • | |
| 14 | $C_7H_{15}-$ | cyclohexyl-phenyl | —COO— | $-\overset{O}{\underset{\parallel}{C}}-C_4H_9$ | S | • 59.4 | — | • 67.1 | — | — | — | • | |
| 15 | $C_5H_{11}-O-$ | cyclohexyl-phenyl | —COO— | $-\overset{O}{\underset{\parallel}{C}}-C_4H_9$ | S | • 85.7 | — | — | — | • 97.8 | — | • | |
| 16 | $C_6H_{13}-$ | phenyl-cyclohexyl | —COO— | $-\overset{O}{\underset{\parallel}{C}}-C_4H_9$ | S | • 61.3 | — | • 81.3 | — | • 100.9 | — | • | |

TABLE 1-continued

| Compound No. | In formula (I) R¹ | Ar | B | R² | Absolute configuration | Phase transition point (°C) Cr | SE | SB | Sc* | SA | Ch | Is | Note |
|---|---|---|---|---|---|---|---|---|---|---|---|---|---|
| 17 | $C_8H_{17}-O-$ | (phenyl) | $-COO-$ | $-\overset{O}{\underset{\parallel}{C}}-C_4H_9$ | S | • 42.1 | — | — | — | — | — | • | |
| 18 | $C_{10}H_{21}-O-$ | (phenyl) | $-COO-$ | $-\overset{O}{\underset{\parallel}{C}}-C_4H_9$ | S | • 49.5 | — | — | — | — | — | • | |
| 19 | $C_{12}H_{25}-O-$ | (phenyl) | $-COO-$ | $-\overset{O}{\underset{\parallel}{C}}-C_4H_9$ | S | • 56.4 | — | — | — | — | — | • | |
| 20 | $C_8H_{17}-$ | (cyclohexyl) | $-COO-$ | $-\overset{O}{\underset{\parallel}{C}}-C_4H_9$ | S | • 21.5 | — | — | — | — | — | • | |
| 21 | $C_8H_{17}-O-$ | (fluorophenyl-phenyl) | $-COO-$ | $-\overset{O}{\underset{\parallel}{C}}-C_4H_9$ | S | • 81.3 | — | — | • 94.5 | • 119.8 | — | • | Example 3 |
| 22 | $C_8H_{17}-O-$ | (biphenyl) | $-COO-$ | $-\overset{O}{\underset{\parallel}{C}}-OC_4H_9$ | S | • 95.2 | — | • 102.1 | — | • 145.4 | — | • | Example 4 |
| 23 | $C_9H_{19}-$ | (biphenyl) | $-CH_2O-$ | $-\overset{O}{\underset{\parallel}{C}}-OC_4H_9$ | S | • 94 | — | — | — | — | — | • | Example 5 |
| 24 | $C_8H_{17}-O-$ | (biphenyl) | $-CH_2O-$ | $-\overset{O}{\underset{\parallel}{C}}-C_4H_9$ | S | • 104.3 | — | — | • 105.0 | • 112.7 | — | • | Example 5 |

TABLE 1-continued

| Compound No. | In formula (I) R¹ | Ar | B | R² | Absolute configuration | Phase transition point (°C.) Cr | SE | SB | Sc* | SA | Ch | Is | Note |
|---|---|---|---|---|---|---|---|---|---|---|---|---|---|
| 25 | $C_8H_{17}-$ | (pyrimidine-phenyl) | $-COO$ | $-\overset{O}{\underset{\|}{C}}-\overset{*}{C}H-OC_4H_9$ (S), $CH_3$ | S | • 53.3 | — | — | — | • 96.2 | — | • | *1 |
| 26 | $C_7H_{15}-$ | (cyclohexyl-phenyl) | $-COO$ | $-\overset{O}{\underset{\|}{C}}-\overset{*}{C}H-OC_4H_9$ (S), $CH_3$ | S | *2 | — | • 34.4 | — | • 51.7 | — | • | |
| 27 | $C_{12}H_{25}-O-$ | (fluorophenyl) | $-COO$ | $-\overset{O}{\underset{\|}{C}}-\overset{*}{C}H-OC_4H_9$ (S), $CH_3$ | S | • 27.0 | — | — | — | — | — | • | |
| 28 | $C_8H_{17}-O-$ | (phenyl) | $-COO$ | $-\overset{O}{\underset{\|}{C}}-\overset{*}{C}H-OC_4H_9$ (S), $CH_3$ | S | • 23.0 | — | — | — | — | (• 7.4) | • | |

Note
*1 When R² has an optical activity, a sign in ( ) on the right side of R² shows the absolute configuration thereof.
*2 m.p. is not observed down to −40° C.

The specific feature of the compound of the present invention consist in that when it exhibits ferroelectric liquid crystal phases by itself, it is naturally preferred as a component of ferroelectric liquid crystal compositions, but even when it exhibits no ferroelectric liquid crystal phase, it is also preferred as a component of ferroelectric liquid crystal compositions. Further, when the compound of the present invention is added in a suitable quantity to an achiral or chiral liquid crystal compound or composition, the resulting ferroelectric liquid crystal compositions have a far larger spontaneous polarization value (hereinafter abbreviated to Ps) than that prior to the addition. When ferroelectric liquid crystals are made up into a display element, it is said that its Ps is in inverse proportion to its response time. Thus, the larger the Ps, the shorter the response time. Since liquid crystal compounds or compositions exhibiting phases such as achiral smectic C, etc. are not ferroelectric liquid crystals, there is no Ps. However, compositions obtained by adding the compound of the present invention to the above substances exhibit ferroelectric liquid crystal phases, and the Ps notably increases depending on the quantity thereof added. Further, substances obtained by adding the compound of the present invention in a suitable quantity to ferroelectric liquid crystal compounds or compositions Ps of which is very small, have a notably increased Ps; hence the response time also becomes shorter than that prior to the addition. Namely, the compound of the present invention is preferred as a component bearing the Ps of ferroelectric liquid crystal compositions.

The compound of the formula (I) of the present invention can be classified into the following groups of compounds:

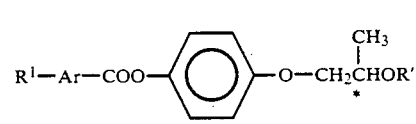
(I-a)

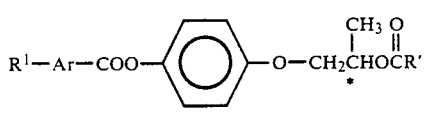
(I-b)

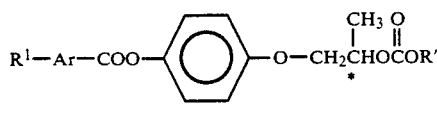
(I-c)

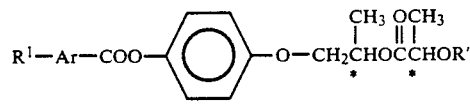
(I-d)

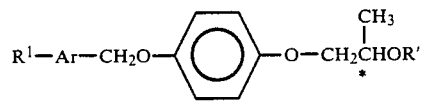
(I-e)

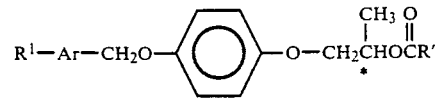
(I-f)

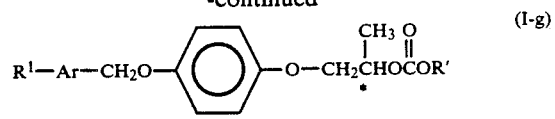
(I-g)

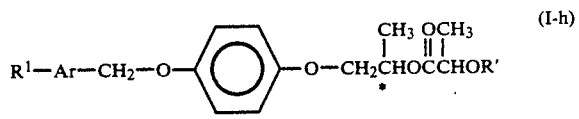
(I-h)

In these formulas, $R^1$, Ar and * are as defined above and R' represents a linear or branched chain alkyl group of 1 to 14 carbon atoms.

Among the above illustrated compounds, those having a molecular structure of

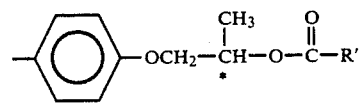

in the molecule as in the compounds (I-b) and (I-f) and those having a molecular structure of

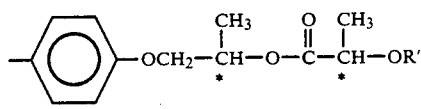

in the molecule as in the compound (I-d) and (I-h), each exhibit a particularly large spontaneous polarization value, as described later in Examples 6, 7 and 8 and those having a structure of

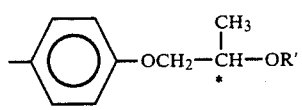

in the molecule as in the compound (I-a) and (I-e) and those having a structure of

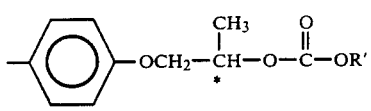

in the molecule as in the compounds (I-c) and (I-g), when they are added to a nematic liquid crystal composition, each have a specific feature of notably flattening the temperature dependency of the chiral pitch of the resulting chiral nematic liquid crystal composition or making the temperature dependency negative (see Examples 9 and 10).

As to most of chiral substances currently used for being added to nematic liquid crystals, the chiral pitch thereof becomes longer with rise of temperature, but to the contrary, those of which the chiral pitch becomes shorter with rise of temperature have been reported, and it has been known that these substances reduce the temperature change in the threshold voltage as an electro-optic specific feature of TN type display elements (see The 33rd Associated Lecture Meeting related to Applied Physics (1986, spring), Collected Lecture Preprints 1 p-G-7 (page 78), and Japan Display '86, Collected Lecture Preprints 8.3 (pages 286–289)).

Since the compound of the present invention has physical properties similar thereto, it is possible to reduce the temperature change in the threshold voltage of chiral nematic liquid crystal compositions obtained by adding the compound.

Further, separately, in the case of the so-called super TN type display, having the twist angle changed to 180–270°, the temperature change in the pitch notably reduces the display quality, but in the case where a chiral nematic liquid crystal composition obtained by adding the compound of the present invention to the super TN type display is used, it is possible to prepare an excellent super TN type display element the display quality of which is not damaged by temperature change.

As described above, the compound of the present invention is useful not only as a component bearing the PS of ferroelectric liquid crystal compositions, but also as a chiral component compound for chiral nematic compositions.

Preparation of the compound of the present invention will be described in the order of (I-a) to (I-h).

_Preparation of (I-b):_

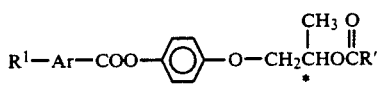

_Preparation of (I-c):_

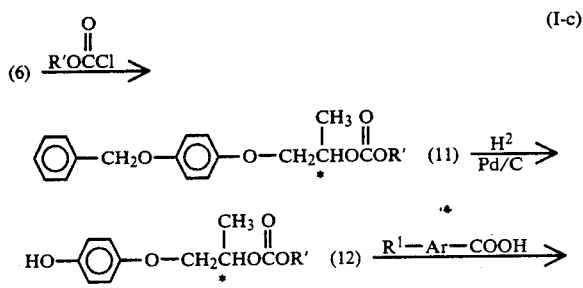

_Preparation of (I-a):_

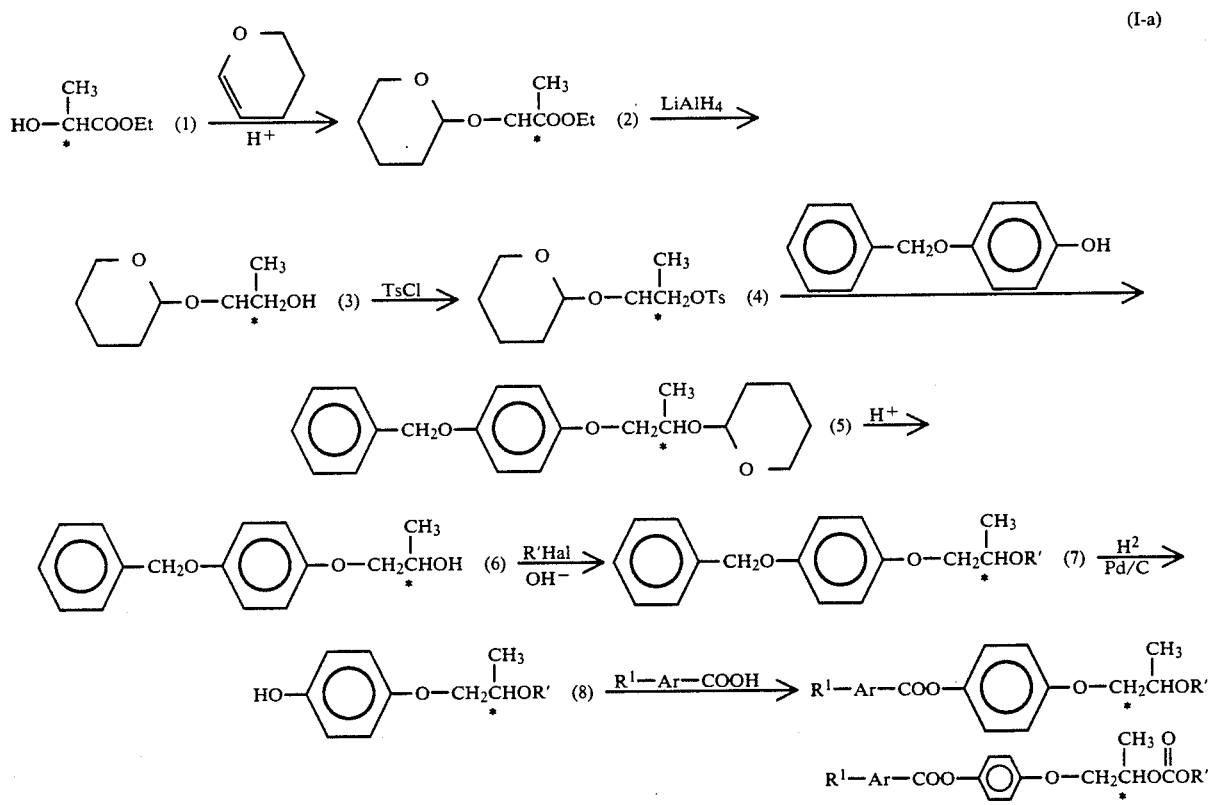

_Preparation of (I-b):_

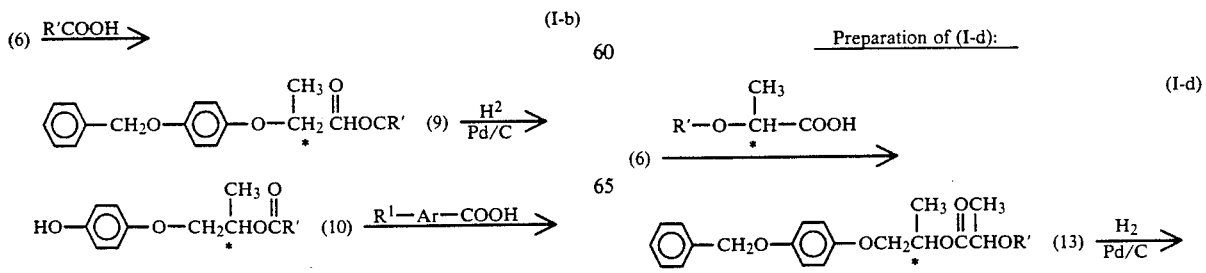

_Preparation of (I-d):_

-continued
Preparation of (I-d):

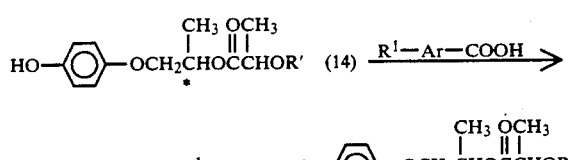

Preparation of (I-e):

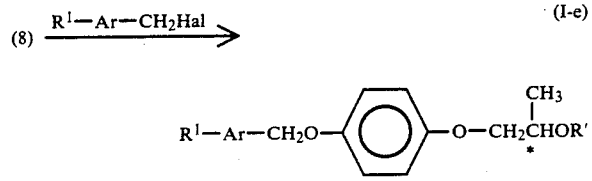

Preparation of (I-f):

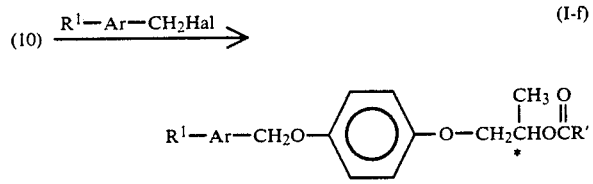

Preparation of (I-g):

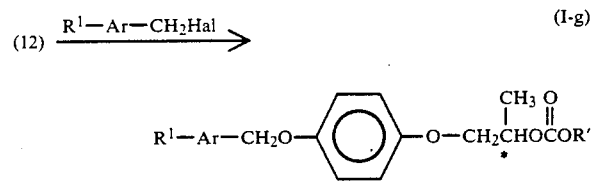

Preparation of (I-h):

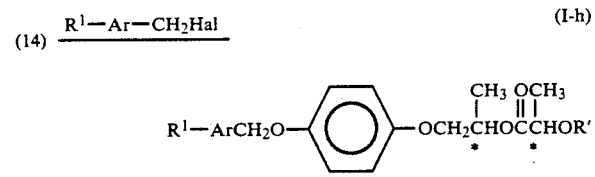

In the above formulas, $R^1$, Ar, R' and * are as defined above, Ts represetns p-toluenesulfonyl group and Hal represetns halogen atom.

The compound and liquid crystal composition of the present invention will be described in more detail by way of Examples.

EXAMPLE 1

Preparation of S-(p-(2-ethoxy-propoxy)-phenyl)-4'-octyloxy-4-biphenyl)-carboxylate (a compound of the formula (I) wherein $R^1$ represents octyloxy, Ar represents

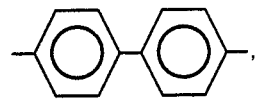

$R^2$ represents ethyl and A represents -COO-)

(i) Preparation of S-2-(2'-tetrahydropyranyloxy)-1-(p-toluenesulfonyloxy)-propane A mixture of S-2-tetrahydropyranyloxy-1-propanol (137 g) prepared according to a method described in C. Malanga et al, Synthetic Communications 12 (1), 67–70(1982) with anhydrous pyridine (600 g) was cooled with ice, followed by dropwise adding a solution of p-toluenesulfonyl chloride (165 g) in pyridine (200 ml) to the mixture, adding toluene (1 l) after completion of the reaction, washing the resulting material with water, drying and distilling off the solvent to obtain S-2-(2'-tetrahydropyranyloxy)-1-(p-toluenesulfonyloxy)propane (257 g).

(ii) Preparation of S-1-(p-benzyloxyphenoxy)-2-propanol

Tetrahydrofuran (hereinafter abbreviated as THF) (20 ml) was added to sodium hydride (60%) (3.6 g), followed by cooling the mixture with ice, adding thereto a solution of p-benzyloxyphenol (14 g) in THF (200 ml), adding to the mixture, a solution of the tosylated product prepared in the above paragraph (i) (20 g) in N,N-dimethylformamide (hereinafter abbreviated as DMF) (200 ml), agitating the mixture at 60° C. for 6 hours, further adding toluene (300 ml), washing the mixture with water, then with an alkali and further with water, drying, distilling off the solvent, adding the residue, pyridium-p-toluenesulfonate (hereinafter abbreviated to PPTS) (1.5 g), adding ethanol (100 ml), agitating the mixture on a water bath at 60° C. for one hour, distilling off ethanol, adding toluene (300 ml) to the residue, washing the mixture with an acid, then with an alkali and further with water, drying, distilling off the solvent and recrystallizing the residue from a mixed solvent of heptane with toluene (3:1) to obtain S-1-(p-benzyloxy-phenoxy)-2-propanol (m.p. 96–98° C.) (8 g).

(iii) Preparation of S-p-(p-benzyloxy)-(2-ethoxy-propoxy)benzene

THF (50 ml) was added to sodium hydride (60%) (0.75 g), followed by adding thereto S-1-(p-benzyloxy-phenoxy)-2-propanol prepared in the above paragraph (ii) (3.4 g), further adding a solution of ethyl iodide (2.6 g) in DMF (100 ml), heating the mixture at 60° C. for 6 hours, adding toluene (200 ml), washing the mixture with an acid, then with an alkali and further with water, drying, and purifying the resulting material according to chromatography using a column having activated alumina filled therein to obtain oily S-p-(p-benzyloxy)-(2-ethoxy-propoxy)-benzene (3.6 g).

(iv) Preparation of S-p-(2-ethoxy-propoxy)-phenol

S-p-(p-Benzyloxy)-(2-ethoxy-propoxy)-benzene obtained in the above paragraph (iii) (3.6 g) was subjected to hydrogenolysis using 5% paradium-carbon catalyst (0.5 g) in ethanol, followed by filtering off the catalyst and distilling off the solvent to obtain S-p-(2-ethoxy-propoxy)-phenol (2.8 g).

(v) Preparation of the captioned compound

A mixture of S-p-(2-ethoxy-propoxy)-phenol obtained in the above paragraph (iv) (0.3 g), 4'-octyloxy-4-biphenyl-carboxylic acid (0.45 g), N,N-dicyclohexyl-carbodiimide (hereinafter abbreviated as DCC) (0.5 g), 4-N,N-dimethylaminopyridine (hereinafter abbreviated as DMAP) (0.1 g) and anhydrous dichloromethane (50 ml) was agitated at room temperature for 8 hours, followed by filtering off deposited solids, washing the mother liquor with an acid, then with an alkali and further with water, drying and purifying the resulting material according to column chromatography using a column having activated alumina filled therein to obtain the captioned S-(p-(2-ethoxy-propoxy)-phenyl)-(4'-octyloxy-4-biphenyl)-carboxylate (0.3 g).

This product exhibited the following phase transition points (unit: °C.; this applies to the subsequent):
Cr→SB 73.0, SB→SC* 100.0, SC*→SA 132.5, SA→$I_{so}$ 176.0 wherein Cr, SB, SC*, SA and Iso are abbreviations of crystalline phase, smectic B phase, chiral smectic C phase, smetic A phase and isotropic phase, respectively (this applies also to the subsequent portions of this application).

S-(p-(2-Ethoxy-propoxy)-phenyl)-(4'-octyl-4-biphenyl)-carboxylate was obtained in the same manner as the above. This product exhibited the following phase transition points: Cr→SB 73.0, SB→SA 91.8 and SA→Iso 139.8.

EXAMPLE 2

Preparation of S-(p-(2-heptanoyloxy-propoxy)-phenyl)-(4'-octyloxy-4-biphenyl)-carboxylate (a compound of the formula (I) wherein $R^1$ represents octyloxy, Ar represents

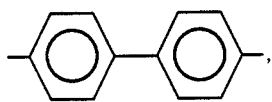

$R^2$ represents heptanoyl and A represents -COO-)

(i) Preparation of S-p-(2-heptanoyloxy-propoxy)-phenol

A mixture of S-1-(p-benzyloxy-phenoxy)-2-propanol obtained in Example 1-(ii) (1.3 g), heptanoic acid (0.8 g), DCC (1.8 g), DMAP (0.1 g) and anhydrous dichloromethane (50 ml) was agitated at room temperature for 6 hours, followed by filtering off deposited solids, washing the mother liquor with an acid, then with an alkali and further with water, drying, purifying the resulting material according to column chromatography using a column having activated alumina filled therein and recrystallizing from ethanol to obtain S-p-(p-benzyloxy)-(2-heptanoyloxy-propoxy)-benzene (1.45 g) having a m.p. of 43.6-44.9° C. This product was subjected to hydrogenolysis using 5%-paradium-carbon catalyst in ethanol, followed by filtering off the catalyst and distilling off the solvent to obtain S-p-(2-heptanoyloxy-propoxy)-phenol (0.8 g).

(ii) Preparation of the captioned compound

Using S-p-(2-heptanoyloxy-propoxy)-phenol (0.4 g) obtained in the above paragraph (i), 4'-octyloxy-4-biphenyl-carboxylic acid (0.4 g), DCC (0.5 g), DMAP (0.1 g) and anhydrous dichloromethane (50 ml), S-(p-(2-heptanoyloxy-propoxy)-phenyl)-(4'-octyloxy-4-biphenyl) -carboxylate (0.3 g) was obtained in the same manner as in Example 1-(v). This product exhibited the following phase transition points:
Cr→SA 108 and SA→$I_{so}$ 139.

The following compounds were prepared in the same manner as the above:

S-(p-(2-Butanoyloxy-propoxy)-phenyl)-(4'-hexyloxy-4-biphenyl)-carboxylate

This product exhibited the following phase transition points:
Cr→SB 97.4, SB→SA 108.9, SA→$I_{so}$ 163.8, and in the temperature-descending process, SB→SE 82.4.

S-(p-(2-Butanoyloy-propoxy)-phenyl)-(4'-nonyl-4-bipyenyl)-carboxylate

This product exhibited phase transition points of Cr→SB 74.1, SB→SA 79.6 and SA→$I_{so}$ 115.9.

S-(p-(2-Pentanoyloxy-propoxy)-phenyl)-(4'-decyloxy-4-biphenyl)-carboxylate

This product exhibited phase transition points of Cr→SC* 108.1, SC*→SA 137.8 and SA→$I_{so}$ 137.8.

S-(p-(2-Pentanoyloxy-propoxy)-phenyl)-(4'-heptyl-4-biphenyl)-carboxylate

This product exhibited phase transition points of Cr→SB 67.9, SB→SA 88.8 and SA→Iso 117.7.

EXAMPLE 3

Preparation of S-(p-(2-pentanoyloxy-propoxy)-phenyl)-(3'-fluoro-4'-octyloxy-4-biphenyl)carboxylate (a compound of the formula (I) wherein $R^1$ represents octyloxy, Ar represents

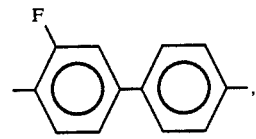

represents pentanoyl and A represents -COO-)

Using S-p-(2-pentanoyloxy-propoxy)-phenol (m.p. 62.1-64.1) prepared in the same manner as in Example 2-(i), 3'-fluoro-4'-octyloxy-4-biphenylcarboxylic acid, DCC and DMAP were reacted in the same manner as in Example 1-(v), S-(p-(2-pentanoyloxy-propoxy)-phenyl)(3'-fluoro-4'-octyloxy-4-biphenyl)-carboxylate was obtained.

This product exhibited phase transition points of Cr→SC* 81.3, SC*→SA 94.5 and SA→Iso 119.8.

EXAMPLE 4

Preparation of S-(p-(2-butoxycarbonyloxy-propoxy)-phenyl)-(4'-octyloxy-4-biphenyl)-carboxylate (a compound of the formula (I) wherein $R^1$ represents octyloxy, Ar represents

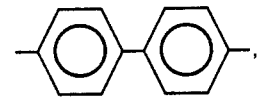

$R^2$ represents butoxycarbonyl and A represents -COO-

S-1-(p-Benzyloxy-phenoxy)-2-(butoxycarbonyloxy)-propane (m.p. 50.4-50.9° C.) obtained by reacting S-1-(p-benzyloxy-phenoxy)-2-propanol obtained in Example 1-(ii) with butyl chloroformate in pyridine solvent, was subjected to hydrogenosis reaction using a paradium-carbon catalyst in pyridine solvent to obtain p-(2-(butoxycarbonyloxy)-propoxy)-phenol. This phenol (0.5 g), 4'-octyloxy-4-biphenyl-carboxylic acid (0.5 g), DCC (0.6 g), DMAP (0.1 g) and dichloromethane (50 ml) were reacted in the same manner as in Example 1-(v), followed by purification to obtain S-(p-(2-butoxycarbonyloxy-propoxy)-phenyl)-(4'-octyloxy4-biphenyl)-carboxylate (0.4 g). This product exhibited phase transition points of Cr→SB 95.2, SB→SA 102.1, SA→I$_{so}$ 145.4° C., and in the temperature-descending process, SB→SE 67.9.

EXAMPLE 5

Preparation of 4'-octyl-4-(4-(2-(butoxycarbonyloxy)-propoxy)-phenoxymethyl)-biphenyl (a compound of the formula (I) wherein R$^1$ represents octyl, Ar represents

R$^2$ represents butoxycarbonyl and A represents -CH$_2$O-)

A solution of p-(2-(butoxycarbonyloxy)-propoxy)-phenol (1 g) prepared in Example 4 in tetrahydrofuran (20 ml) was dropwise added to a suspension of sodium hydride (0.2 g) in tetrahydrofuran, followed by dropwise adding to the mixture, a solution of 4'-octyl-4-chloromethylbiphenyl (1.2 g) in dimethylformamide (50 ml), agitating the mixture at 60° C. for 10 hours, pouring the reaction solution in water, extracting the resulting material with toluene (300 ml), washing the extract with an acid, then with an alkali and further with water, purifying it according to column chromatography using a column having activated alumina filled therein and recrystallizing from a mixed solvent of ethyl acetate with ethanol to obtain the objective 4'-octyl-4-(4-(2-(butoxycarbonyloxy)-propoxy)-phenoxymethyl)-biphenyl (0.5 g) having a m.p. of 94° C.

The following compound was prepared in the same manner as the above:

4'-octyloxy-4-(4-(2-(butanoyloxy)-propoxy)phenoxymethyl)-biphenyl

This product exhibited phase transition points of Cr→SC* 104.3, SC*→SA 105.0 and SA→I 112.7.

EXAMPLE 6 (USE EXAMPLE 1)

S-(p-(2-Pentanoyloxy-propoxy)-phenyl)-(3'-fluor4'-octyloxy-4-biphenyl)-carboxylate (compound of Example 3) was filled in a cell of ca. 2 μm thick provided with transparent electrodes each obtained by coating PVA (polyvinyl alcohol) onto the surface and rubbing the resulting surface to subject it to a parallel aligning treatment, followed by placing the resulting liquid crystal cell between two sheets of crossed polarizers, impressing an alternating current voltage of a low frequency of 40 Hz and 10 V and observing the resulting cell. A clear switching operation having a very good contrast was observed. The spontaneous polarization value (Ps) (according to Sowyer-Tower method) and the response time at that time were as follows:

| t (°C.) | Ps (nC/cm$^2$) | Response time (μ sec) |
| --- | --- | --- |
| 90° C. | 94 | 8 |
| 80 | 144 | 12 |
| 70 | 178 | 16 |

As illustrated above, among the compounds of the formula (I), those which singly exhibit SC* phase have a large Ps and a short response time; hence the above compounds are useful not only singly, but also as a component of liquid crystal compositions.

EXAMPLE 7 (USE EXAMPLE 2)

A liquid crystal composition (A) consisting of

| | |
| --- | --- |
| $C_6H_{13}$—O—⟨phenyl⟩—⟨pyrimidine⟩—$C_8H_{17}$ | 30 wt. % |
| $C_8H_{17}$—O—⟨phenyl⟩—⟨pyrimidine⟩—$C_8H_{17}$ | 20 wt. % |
| $C_9H_{19}$—O—⟨phenyl⟩—⟨pyrimidine⟩—$C_8H_{17}$ | 10 wt. % |
| $C_{10}H_{21}$—O—⟨phenyl⟩—⟨pyrimidine⟩—$C_8H_{17}$ | 10 wt. % |
| $C_6H_{13}$—⟨phenyl⟩—⟨phenyl⟩—⟨pyrimidine⟩—$C_8H_{17}$ | 20 wt. % |
| $C_7H_{15}$—⟨phenyl⟩—⟨phenyl⟩—⟨pyrimidine⟩—$C_8H_{17}$ | 10 wt. % | exhibits phase transition points of Cr→SC 4, SC→SA 65, SA→Ne 79 and Ne→I$_{so}$ 90. However, since this liquid crystal composition (A) is not a ferroelectric liquid crystal, no Ps is present.

Whereas, a mixture of this composition A (90% by weight) with the compound of the present invention,

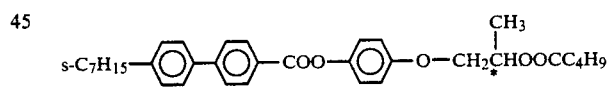

(10% by weight), namely a liquid crystal composition (B) exhibited phase transition points of SC*→SA 39.2, SA→ch 82.3 and ch→Iso 90.7. Its switching operation was observed under the same conditions as in Example 6. The results were as follows:

| t (°C.) | Ps (nC/cm$^2$) | Response time (μ sec) |
| --- | --- | --- |
| 35 | 1.3 | 80 |
| 25 | 1.9 | 180 |
| 15 | 1.9 | 300 |

As illustrated above, it has been elucidated that by adding the compound of the formula (I) of the present invention to an achiral smectic liquid crystal composition, it is possible to impart Ps and a ferroelectric liquid crystal composition having a short response time is obtained.

EXAMPLE 8 (USE EXAMPLE 3)

A mixture of 90% by weight of composition A which was prepared according to Example 7 and 10% by weight of the compound of the present invention (compound No. 28)

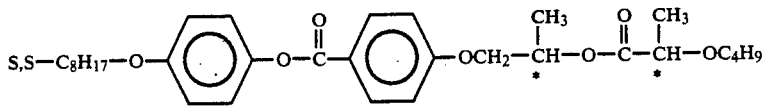

namely a composition C showed phase transition points as follows.

SC*→SA 42.0° C., SA→Ch 72.5° C., Ch→Is 84.2° C. Its switching operation was observed under the same conditions as in Example 6. The results were as follows.

| t (°C.) | Ps (nC/cm$^2$) | Response time ($\mu$ sec) |
| --- | --- | --- |
| 32 | 4.7 | 86 |
| 25 | 5.8 | 138 |

EXAMPLE 9 (USE EXAMPLE 4)

A compound of the present invention,

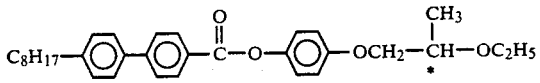

(1% by weight) was added to a nematic liquid composition (ZLI 1132, a commercially available product manufactured by Merck Company) to prepare a chiral nematic liquid crystal composition. This composition was filled in a wedge type cell subjected to a parallel treatment, followed by observing the resulting cell under a polarizing microscope. As a result, the resulting heclical pitch was observed as follows and its temperature dependency was negative:

| Temperature (°C.) | 20 | 30 | 40 | 50 | 60 | 70 |
| --- | --- | --- | --- | --- | --- | --- |
| Pitch length ($\mu$m) | 28.0 | 27.9 | 27.6 | 27.0 | 26.0 | 23.5 |

EXAMPLE 10 (USE EXAMPLE 5)

Employing the same method as in Example 9, the compound of the present invention,

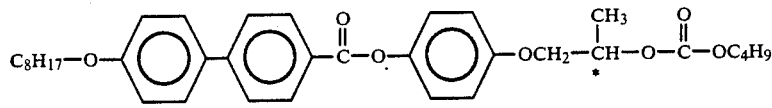

was observed. As a result, its helical pitch was observed as follows:

| Temperature (°C.) | 20 | 30 | 40 | 50 | 60 | 70 |
| --- | --- | --- | --- | --- | --- | --- |
| Pitch length ($\mu$m) | 13.0 | 13.0 | 13.0 | 13.0 | 12.9 | 12.3 |

As described above, the temperature dependency of pitch was very flat or negative; hence it has been found that the compound of the present invention is a superior agent for adjusting the pitch of chiral nematic liquid crystal compositions.

According to the present invention, it is possible to obtain capable of shortening the response time of liquid crystal display elements, and by adding this compound to an achiral or chiral smectic liquid crystal compound and/or composition, it is possible to increase the Ps of the resulting ferroelectric liquid crystal composition and also shorten the response time thereof.

What we claim is:

1. A liquid crystalline compound of the formula (I)

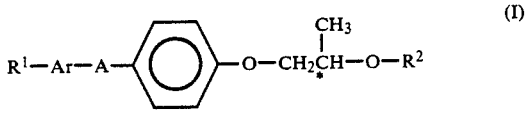

wherein $R^1$ represetns linear chain alkyl or alkoxy, each of 1 to 18 carbon atoms; Ar represents

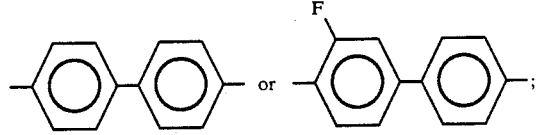

A represents -COO- or -CH$_2$O-; $R^2$ represents alkanoyl of 2 to 18 carbon atoms, alkoxycarbonyl of 3 to 18 carbon atoms or 2-alkoxypropanoyl of 4 to 18 carbon atoms; and C having the symbol * attached thereto represents an asymmetric carbon atom.

2. A compound according to claim 1 wherein $R^1$ is linear chain alkoxy of 1-18 carbon atoms, Ar is

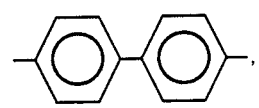

A is -COO-, and $R^2$ is alkanoyl of 2 to 18 carbon atoms.

3. A compound according to claim 1, wherein $R^1$ represents alkyl or alkoxy each of 5 to 10 carbon atoms, and $R^2$ represents alkanoyl of 2 to 7 carbon atoms.

4. A compound according to claim 1, wherein $R^1$ represents alkyl or alkoxy each of 5 to 10 carbon atoms, and $R^2$ represents 2-alkoxypropanoyl of 4 to 8 carbon atoms.

5. A compound according to claim 1, wherein $R^1$ represents alkyl or alkoxy each of 5 to 10 carbon atoms, and $R^2$ represents alkoxycarbonyl of 3 to 18 carbon atoms.

6. A chiral smectic liquid crystal composition comprising at least two components at least one of which is a compound of formula (I) set forth in claim 1.

7. A chiral nematic liquid crystal composition comprising at least two components at least one of which is a compound of formula (I) set forth in claim 1.

8. A compound of the formula (I)

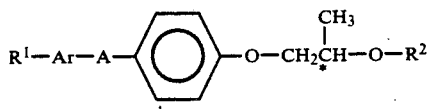

wherein $R^1$ represents linear chain alkyl or alkoxy, each of 1 to 18 carbon atoms; Ar represents

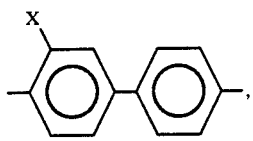

wherein X represents hydrogen or halogen; A represents -COO- or -CH$_2$O-; $R^2$ represetns alkanoyl of 2 to 15 carbon atoms or alkoxycarbonyl of 3 to 15 carbon atoms; and C having the symbol * attached thereto represetns an asymmetric carbon atom.

* * * * *